(12) United States Patent
Kim et al.

(10) Patent No.: US 9,546,772 B2
(45) Date of Patent: Jan. 17, 2017

(54) ROD LENS FOR LIGHTING APPARATUS, LIGHTING APPARATUS INCLUDING THE SAME AND SEMICONDUCTOR MANUFACTURING METHOD USING THE APPARATUS

(71) Applicant: Samsung Electronics Co., Ltd., Suwon-si (KR)

(72) Inventors: Kwang-soo Kim, Pyeongtaek-si (KR); Wook-rae Kim, Suwon-si (KR); Tae-joong Kim, Hwaseong-si (KR); Byeong-hwan Jeon, Yongin-si (KR)

(73) Assignee: SAMSUNG ELECTRONICS CO., LTD., Samsung-ro, Yeongtong-gu, Suwon-si, Gyeonggi-do (KR)

( * ) Notice: Subject to any disclaimer, the term of this patent is extended or adjusted under 35 U.S.C. 154(b) by 0 days.

(21) Appl. No.: 14/601,234

(22) Filed: Jan. 21, 2015

(65) Prior Publication Data

US 2015/0226398 A1 Aug. 13, 2015

(30) Foreign Application Priority Data

Feb. 11, 2014 (KR) ........................ 10-2014-0015650

(51) Int. Cl.
*G02B 3/00* (2006.01)
*F21V 5/04* (2006.01)
(Continued)

(52) U.S. Cl.
CPC .............. *F21V 5/04* (2013.01); *G01N 21/8806* (2013.01); *H01L 22/12* (2013.01); *G02B 2003/0093* (2013.01)

(58) Field of Classification Search
CPC .................... G02B 3/00; G02B 3/0006; G02B 3/005–3/0068; G02B 2003/0093; G02B 6/0011; G02B 6/24; G02B 6/26; G02B 6/27–6/272; G02B 21/00; G02B 21/0004; G02B 21/0016; G02B 21/06; G02B 21/08; G02B 21/18; G02B 27/09; G02B 27/095–27/0966; G02B 27/10; G02B 27/1066; G02B 27/12–27/126; F21V 5/00; F21V 5/04; F21V 5/043; F21V 5/045; F21V 5/08; G01N 21/88; G01N 21/89; G01N 21/95–21/9505; G01N 2021/9513; H01L 22/00; H01L 22/10; H01L 22/12; H01L 22/30
(Continued)

(56) References Cited

U.S. PATENT DOCUMENTS 5,081,346 A * 1/1992 Narabu ..................... H04N 1/03
  250/208.1
6,545,814 B2 * 4/2003 Bartlett ................ G02B 27/143
  348/148
(Continued)

FOREIGN PATENT DOCUMENTS

JP 62054846 A * 3/1987
JP 2001156359 A * 6/2001
(Continued)

OTHER PUBLICATIONS

Website for IRD Glass, <http://irdglass.com/products/cylindrical-optics/rod-lens/> retrieved on May 13, 2016 from Wayback Machine archive from Nov. 18, 2012, retrieval address <https://web.archive.org/web/20121118092737/http://irdglass.com/products/cylindrical-optics/rod-lens/>.*

*Primary Examiner* — Derek S Chapel
(74) *Attorney, Agent, or Firm* — Muir Patent Law, PLLC

(57) ABSTRACT

A rod lens for a lighting apparatus and a lighting apparatus including the rod lens are disclosed. The rod lens having a rectangular rod structure extends lengthwise and includes a first end and a second end opposing each other. The first end
(Continued)

is a light incident surface and formed of one continuous surface. The second end is a light exit surface and formed of a plurality of separated surfaces.

17 Claims, 9 Drawing Sheets

(51) Int. Cl.
  *H01L 21/66* (2006.01)
  *G01N 21/88* (2006.01)
(58) Field of Classification Search
  USPC ............... 359/362–363, 385, 618–621, 625, 359/796–797
  See application file for complete search history.

(56) References Cited

U.S. PATENT DOCUMENTS

| | | | |
|---|---|---|---|
| 6,698,891 B2 | 3/2004 | Kato | |
| 6,714,353 B2 | 3/2004 | Park et al. | |
| 6,843,591 B1 * | 1/2005 | Peng | G02B 6/0006 359/618 |
| 6,870,683 B2 | 3/2005 | Park | |
| 7,567,384 B2 * | 7/2009 | Peterson | G02B 5/04 353/31 |
| 7,751,670 B2 * | 7/2010 | Shin | G02B 6/04 353/122 |
| 2002/0017600 A1 | 2/2002 | Ikeda | |
| 2002/0094162 A1 * | 7/2002 | Li | G02B 6/327 385/34 |
| 2003/0081897 A1 | 5/2003 | Itoh et al. | |
| 2005/0185140 A1 | 8/2005 | Matsubara et al. | |
| 2009/0091734 A1 * | 4/2009 | Visser | G02B 27/0905 355/67 |
| 2013/0279851 A1 * | 10/2013 | Matsumoto | G02B 6/327 385/33 |

FOREIGN PATENT DOCUMENTS

| | | | | |
|---|---|---|---|---|
| JP | 2002268000 A | * | 9/2002 | |
| JP | 3610789 | | 10/2004 | |
| JP | 2005090964 | | 4/2005 | |
| JP | 4144532 | | 6/2008 | |
| JP | 2008139707 | | 6/2008 | |
| JP | 2011222594 | | 11/2011 | |
| WO | WO 2014155675 A1 | * | 10/2014 | ........... G03B 21/208 |

* cited by examiner

ROD LENS FOR LIGHTING APPARATUS, LIGHTING APPARATUS INCLUDING THE SAME AND SEMICONDUCTOR MANUFACTURING METHOD USING THE APPARATUS

CROSS-REFERENCE TO RELATED APPLICATIONS

This application claims the benefit of priority to Korean Patent Application No. 10-2014-0015650, filed on Feb. 11, 2014, in the Korean Intellectual Property Office, the disclosure of which is incorporated herein in its entirety by reference.

BACKGROUND

The disclosure relates to a rod lens for a lighting apparatus and a lighting apparatus including the rod lens. The disclosure also relates to a lighting apparatus including a rod lens used to radiate light to an examination object.

Examination processes for discovering small defects are important to improve productivity of a product, such as a semiconductor, a liquid crystal display (LCD), a printed circuit board (PCB), etc. An examination process has been developed to detect smaller defects at higher speeds. In particular, a method of mounting two or more light receiving units has been used to detect smaller defects at higher speeds. This method enables us to examine a greater region in a same amount of time, thereby dramatically reducing examination time.

SUMMARY

The disclosure provides a rod lens for a lighting apparatus. The rod lens is capable of preventing unnecessary light irradiation onto a shadow region between discontinuous examination regions due to structural issues of an examination apparatus when two or more light receiving units are mounted on the examination apparatus. A lighting apparatus including the rod lens is also provided. A manufacturing method of a semiconductor using the lighting apparatus is also provided in this disclosure.

According to an aspect of the inventive concept, there is provided a rod lens for a lighting apparatus. The rod lens has a rectangular rod structure including a first end and a second end opposing each other, wherein the first end is formed of one continuous surface, and the second end is formed of a plurality of separated surfaces. The first end is a light incident surface of the lens. The second end is a light exit surface of the lens.

The second end may be separated to have two surfaces having the same area.

The rod lens may further include: a first lateral face, a second lateral face adjacent to the first lateral face, a third lateral face adjacent to the second lateral face and opposing the first lateral face, and a fourth lateral face adjacent to the third lateral face and opposing the second lateral face, wherein parts of the first lateral face and the third lateral face may be separated to correspond to the two separated surfaces of the second end.

The second end may be separated to have three surfaces having the same area.

The rod lens may further include: a first lateral face, a second lateral face adjacent to the first lateral face, a third lateral face adjacent to the second lateral face and opposing the first lateral face, and a fourth lateral face adjacent to the third lateral face and opposing the second lateral face, wherein parts of the first lateral face and the third lateral face may be separated to correspond to the three separated surfaces of the second bottom surface.

The second end may be separated to have four surfaces having the same area.

The rod lens may further include: a first lateral face, a second lateral face adjacent to the first lateral face, a third lateral face adjacent to the second lateral face and opposing the first lateral face, and a fourth lateral face adjacent to the third lateral face and opposing the second lateral face, Parts of the first lateral face through the fourth lateral face may be separated to correspond to the four separated surfaces of the second end.

According to another aspect of the inventive concept, there is provided a lighting apparatus including: a light source for emitting light; a rod lens positioned to receive the light through an incident surface and send out the light through an exit surface; an objective lens facing an examination object; and a plurality of light receiving units positioned to receive light reflected from the examination object and record an image of the examination object, wherein the incident surface of the rod lens is formed of one continuous surface, and the exit surface of the rod lens is separated into a plurality of surfaces.

The lighting apparatus may further include: a collimator for parallelizing the light incident from the light source to an axis of the rod lens; and a relay unit for reflecting and inverting a wave of light passing through the collimator and transferring the light to the objective lens.

The plurality of light receiving units may include two light receiving units. The exit surface of the rod lens may be separated into two parts and each of the two parts may correspond to one of the two light receiving units.

The two parts of the exit surface of the rod lens may have the same area.

The plurality of light receiving units may include three light receiving units. The exit surface of the rod lens may be separated into three parts and each of the three parts may correspond to one of the three light receiving units.

The three parts of the exit surface may have the same area.

The plurality of light receiving units may include four light receiving units. The exit surface of the rod lens may be separated into four parts and each of the four parts may correspond to one of the four light receiving units.

The exit surface of the rod lens may be vertically and horizontally separated so as to have four parts having the same area.

According to another aspect of the disclosure, there is provided a method manufacturing a semiconductor device, including steps of: forming a semiconductor pattern, an insulator pattern and a metal pattern on a substrate; mounting the substrate on an examination platform of a lighting apparatus; examining a first pattern on the substrate; and determining whether the first pattern passes or fails, wherein, the lighting apparatus comprises, a light source emitting light, a rod lens receiving the light through an incident surface and sending out the light through an exit surface, an objective lens facing the substrate; and a plurality of light receiving units receiving light reflected from the substrate and recording an image of the substrate, wherein the incident surface of the rod lens is formed of one continuous surface, and the exit surface of the rod lens is separated into a plurality of surfaces.

Each surface of the plurality of surfaces of the exit surface may correspond a light receiving unit of the plurality of light receiving units.

The light coming out from the exit surface of the rod lens may irradiate on the substrate, and a shadow region may be formed between the irradiated light patterns which are formed by the plurality of separated exit surfaces of the rod lens.

The recorded image by the plurality of light receiving units may form a shadow region which corresponds to the substrate not recorded by the light receiving units and which is between the regions recorded by the light receiving units.

The manufacturing method may further comprise: examining a second pattern on the substrate; and determining whether the second pattern passes or fails.

The first pattern may be divided into a plurality of portions separated from each other, and the second pattern includes a portion between the portions of the first pattern.

BRIEF DESCRIPTION OF THE DRAWINGS

Exemplary embodiments of the inventive concept will be more clearly understood from the following detailed description taken in conjunction with the accompanying drawings in which.

DETAILED DESCRIPTION

Figure 1:
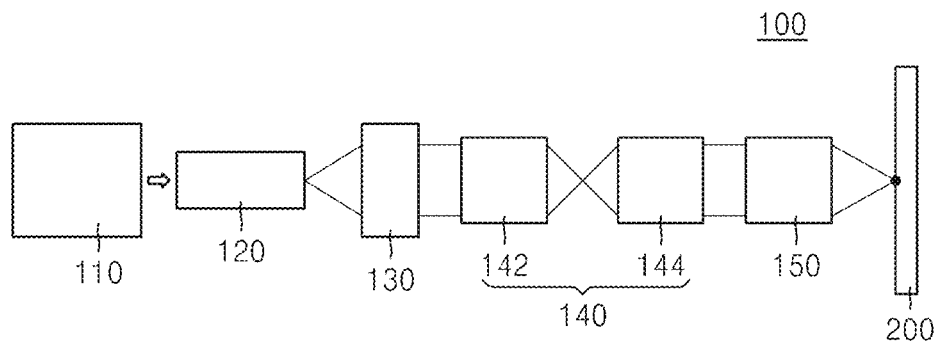
FIG. 1 is a conceptual diagram of a lighting apparatus including a rod lens according to an embodiment of the inventive concept.

Hereinafter, the present disclosure will be described more fully with reference to the accompanying drawings, in which exemplary embodiments of the invention are shown. This invention may, however, be embodied in many different forms and should not be construed as limited to the exemplary embodiments set forth herein. Rather, these embodiments are just that—examples—and many implementations and variations are possible that do not require the details provided herein. It should also be emphasized that the disclosure provides details of alternative examples, but such listing of alternatives is not exhaustive. Furthermore, any consistency of detail between various examples should not be interpreted as requiring such detail—it is impracticable to list every possible variation for every feature described herein. The language of the claims should be referenced in determining the requirements of the invention. Sizes of components in the drawings may be exaggerated for convenience of explanation.

It will be understood that when an element is referred to as being "connected" or "coupled" to another element, it can be directly connected or coupled to the other element or intervening elements may be present. In contrast, when an element is referred to as being "directly connected" or "directly coupled" to another element or "contacting" another element, there are no intervening elements present. Other words used to describe the relationship between elements should be interpreted in a like fashion (e.g., "between" versus "directly between," "adjacent" versus "directly adjacent," "on" versus "directly on," etc.).

It will also be understood that, although the terms first, second, etc. may be used herein to describe various elements, these elements should not be limited by these terms. Unless the context indicates otherwise, these terms are only used to distinguish one element from another. For example, a first element could be termed a second element, and, similarly, a second element could be termed a first element, without departing from the scope of the present invention.

The terminology used herein is for the purpose of describing particular embodiments only and is not intended to be limiting of exemplary embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments described herein will be described referring to plan views and/or cross-sectional views by way of ideal schematic views. Accordingly, the exemplary views may be modified depending on manufacturing technologies and/or tolerances. Therefore, the disclosed embodiments are not limited to those shown in the views, but include modifications in configuration formed on the basis of manufacturing processes. Therefore, regions exemplified in figures may have schematic properties, and shapes of regions shown in figures may exemplify specific shapes of regions of elements to which aspects of the invention are not limited.

Spatially relative terms, such as "beneath," "below," "lower," "above," "upper" and the like, may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 90 degrees or at other orientations) and the spatially relative descriptors used herein interpreted accordingly.

Terms such as "same," "planar," or "coplanar," as used herein when referring to orientation, layout, location, shapes, sizes, amounts, or other measures do not necessarily mean an exactly identical orientation, layout, location, shape, size, amount, or other measure, but are intended to encompass nearly identical orientation, layout, location, shapes, sizes, amounts, or other measures within acceptable variations that may occur, for example, due to manufacturing processes. The term "substantially" may be used herein to reflect this meaning.

Unless otherwise defined, all terms used herein have the same meaning as commonly understood by one of ordinary skill in the art to which exemplary embodiments belong.

FIG. 1 is a conceptual diagram of a lighting apparatus 100 including a rod lens 120 according to an embodiment of the inventive concept.

The lighting apparatus 100 includes a light source 110, the rod lens 120, a collimator 130, a relay unit 140, and an objective lens 150. The lighting apparatus 100 may radiate light generated by the light source 110 onto an examination object 200 to examine a small defect of the examination object 200.

The light source 110 is a light supply source that allows light to be incident to the rod lens 120 and to be radiated onto the examination object 200 via the collimator 130, the relay unit 140, and the objective lens 150. The light source 110 may include a lamp that generates light and a reflector that reflects the light generated by the lamp to the rod lens 120. The light source 110 may be a laser light source that is, for example, an ArF excimer laser, a KrF excimer laser, or a XeCl excimer laser.

The light generated by the light source 110 is incident to the rod lens 120. Although the rod lens 120 has a rectangular shape in FIG. 1, since FIG. 1 is a conceptual diagram, the rod lens 120 may be formed of a substantially long rectangular rod. The rod lens 120 may include an incident surface 120$i$ (see FIGS. 3A through 3C) to which the light generated by the light source 110 is incident and an exit surface 120$f$ (see FIGS. 3A through 3C) through which the light incident to the surface 120$i$ and passing through the rod lens 120 is emitted.

The light emitted through the rod lens 120 is incident to the collimator 130. The collimator 130 is a unit used to collimate the light that is generated by the light source 110, passes through the rod lens 120, and is dispersed, parallel to an axis of the objective lens 150. The collimator 130 is formed in a tube including a slit and a convex lens. The slit may be formed on a focal plane of the rod lens 120. The light comes into the slit and may be changed to parallel light via the collimator 130. The collimator 130 may have a telescope structure having a slit at a primary focal point of the rod lens 120 located a specific distance from the rod lens 120.

According to an embodiment of the inventive concept, the collimator 130 may have a rod lens shape and/or a rod lens structure.

The parallel light output by the collimator 130 reaches the objective lens 150 via a first relay unit 142 and a second relay unit 144. The first relay unit 142 and the second relay unit 144 comprise the relay unit 140. The relay unit 140 transfers the parallel light that comes through the collimator 130 to the objective lens 150 by total internal reflection.

The parallel light transferred by the relay unit 140 reaches the objective lens 150. The objective lens 150 collects and radiates the parallel light onto the examination object 200, thereby facilitating detection of small defects of the examination object 200.

Figure 2:
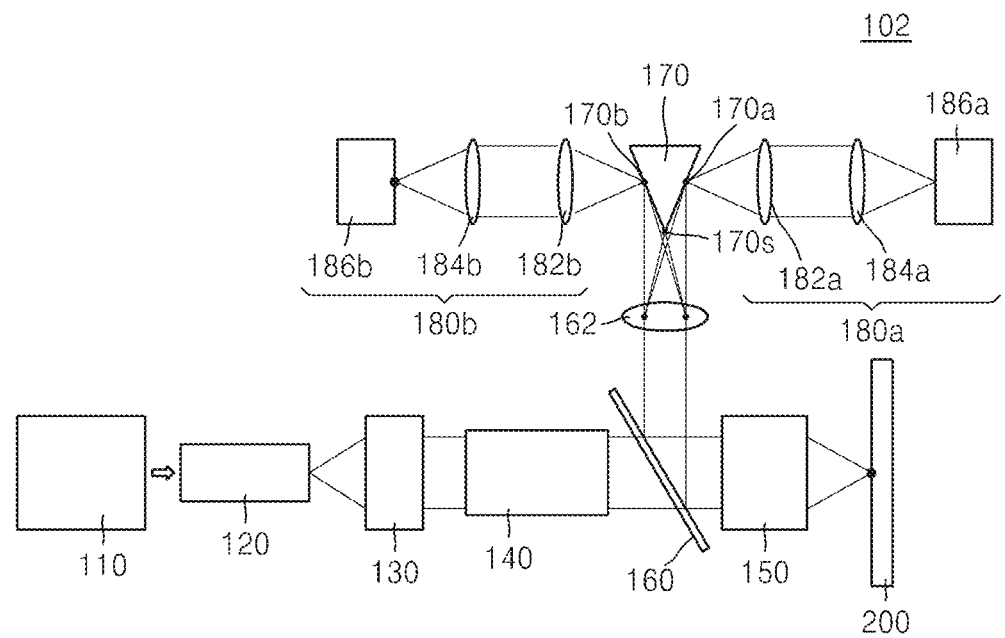
FIG. 2 is a conceptual diagram of a lighting apparatus including a rod lens and multiple light receiving units according to an embodiment of the inventive concept.

FIG. 2 is a conceptual diagram of a lighting apparatus 102 including a rod lens 120 and multiple light receiving units according to an embodiment of the inventive concept.

The lighting apparatus 102 includes a light source 110, a rod lens 120, a collimator 130, a relay unit 140, and an objective lens 150. The light source 110, the rod lens 120, the collimator 130, the relay unit 140, and the objective lens 150 may be the same as those described with reference to FIG. 1 above, and thus descriptions thereof are not repeated.

The lighting apparatus 102 further includes a reflecting plate 160, a polarization separation unit 170, a first focusing optics 180$a$, and a second focusing optics 180$b$, in addition to the above elements.

The light source 110 generates light, and the light comes through the objective lens 150 and is irradiated onto the examination object 200 similarly to the embodiment of FIG. 1. The light comes back through the objective lens 150 after it is reflected on the examination object 200. The reflecting plate 160 changes the direction of the light reflected on the examination object 200 to transmit the light to the polarization separation unit 170.

The light reflected by the reflecting plate 160 reaches the polarization separation unit 170 via a polarization separation lens 162. The polarization separation lens 162 separates the light according to wavelengths and allows the light to reach the first focusing optics 180$a$ and the second focusing optics 180$b$.

The light that passes through the polarization separation lens 162 is separated according to wavelengths and reaches the polarization separation unit 170. According to an embodiment of the inventive concept, the polarization separation unit 170 may be formed of a triangular prism. The light that reaches and is collected at a first surface 170$a$ of the polarization separation unit 170 reaches the first focusing optics 180$a$. The light that reaches and is collected at a second surface 170$b$ of the polarization separation unit 170 reaches the second focusing optics 180$b$.

The first focusing optics 180$a$ includes a first focusing lens 182$a$, a second focusing lens 184$a$, and a first light receiving unit 186$a$. The first focusing lens 182$a$ parallelizes the light collected on the first surface 170$a$ of the polarization separation unit 170 and allows the light to reach the second focusing lens 184$a$. The second focusing lens 184$a$ collects the parallelized light transferred from the first focusing lens 182$a$ to the first light receiving unit 186$a$. The first light receiving unit 186$a$ receives the light collected by the second focusing lens 184$a$ and records the light information as a corresponding surface information of the examination object 200. The first light receiving unit 186$a$ is a unit used to receive images, and record the light reflected from the examination object 200, for example, a charge coupled device (CCD) camera, a complementary metal-oxide semiconductor (CMOS) image sensor, or a lateral buried charge accumulator and sensing transistor array (LBCAST).

The second focusing optics 180b includes a first focusing lens 182b, a second focusing lens 184b, and a second light receiving unit 186b. The second focusing optics 180b is disposed opposite the first focusing optics 180a and performs a function symmetrical to that of the first focusing optics 180a. The second light receiving unit 186b records the information on a remaining part of the examination object 200 that is symmetrical to the part of the examination object 200 recorded by the first light receiving unit 186a.

The light that reaches a third surface 170s of the polarization separation unit 170 may not be reflected in a direction of either the first focusing optics 180a or the second focusing optics 180b. Unlike the light that reaches the first surface 170a and the second surface 170b, the light hitting the third surface 170s may scatter in all directions. Thus, in one embodiment the region corresponding to the light that reaches the third surface 170s cannot be recorded by the first light receiving unit 186a or the second light receiving unit 186b. As described above, when multiple light receiving units are mounted on a lighting apparatus, a continuous examination region may not be formed due to structural issues of the polarization separation unit 170. For example, in certain situations, the light that reaches the third surface 170s among the light that is reflected by the examination object 200 cannot be recorded by a light receiving unit due to diffuse reflection, and a shadow region may be formed in a light irradiation region. Thus, in some cases, the region corresponding to the light that reaches the third surface 170s cannot be recorded by the first light receiving unit 186a or the second light receiving unit 186b.

An examination device for detecting a small defect of several tens nanometers (nm) in length or width should not disregard a small reflection noise, and thus it is very important to limit the light irradiation region to a recording region of the light receiving unit. As described above, light is also irradiated onto the shadow region from the light source 110, and thus unnecessary light may be irradiated onto the shadow region, which causes loss of light, deteriorates light efficiency, and causes reflection noise when the light is reflected from the shadow region. A rod lens 120 according to embodiments of the inventive concept may help to avoid the above-described issues by forming the incident surface 120i (see FIGS. 3A through 3C) as one continuous surface and the exit surface 120f (see FIGS. 3A through 3C) as two discontinuously separate surfaces.

Figure 3A:
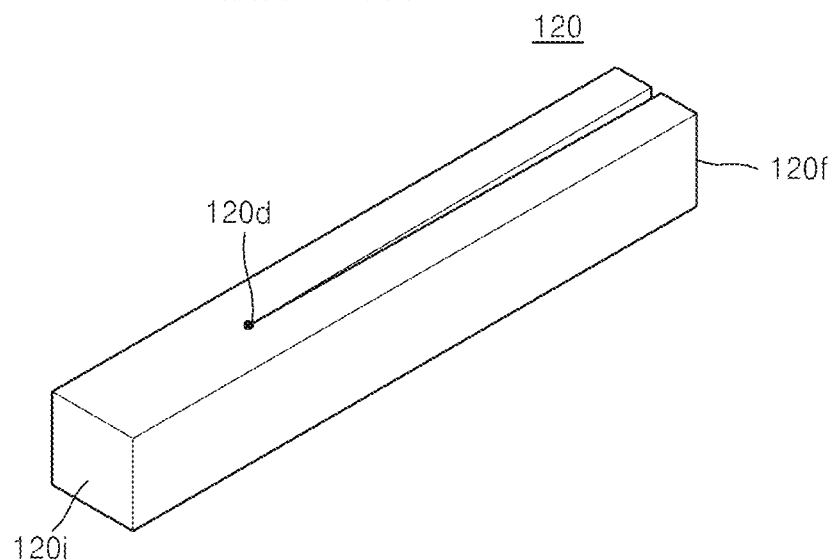
FIGS. 3A and 3B are perspective views of a rod lens for a lighting apparatus according to an embodiment of the inventive concept.
Figure 3B:
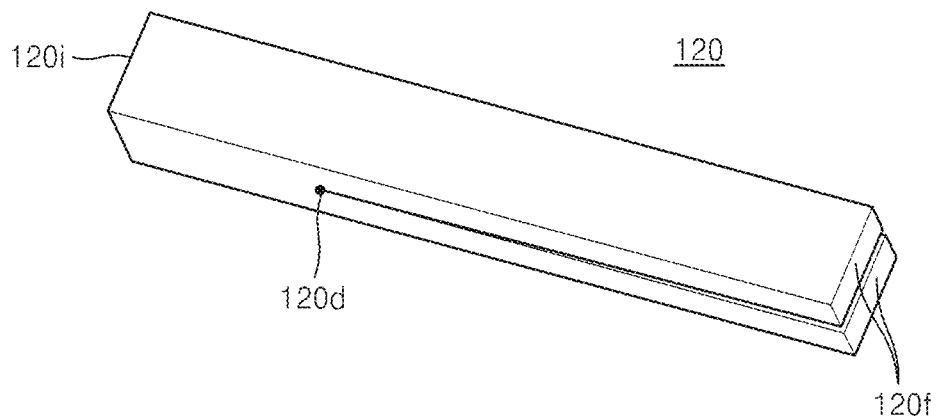

FIGS. 3A and 3B are perspective views of the rod lens 120 according to an embodiment of the inventive concept.

Referring to FIGS. 3A and 3B, the rod lens 120 may be formed of a long rectangular rod. The incident surface 120i of the rod lens 120 is a surface through which light is incident from the light source 110. The incident surface 120i has a rectangular shape or a square surface having no discontinuous surface. The exit surface 120f of the rod lens 120 has a rectangular or square shape having a separated center portion, and opposes the incident surface 120i. For example, the exit surface 120f may be formed of two rectangular surfaces having the same area. According to one embodiment of the inventive concept, the exit surface 120f includes two surfaces having the same area. The exit surface 120f may be formed of surfaces having different areas according to the light beam separation ratios of the polarization separation unit 170 and/or the arrangement and sizes of the multiple light receiving units. Light beam separation ratio is defined as a cross-sectional area of a light beam coming to one surface (for example, surface 170a or 170b) of a polarization separation unit (for example, unit 170) to the whole area of a light beam coming to all of the surfaces (for example, surfaces 170a and 170b).

In one embodiment, the rod lens 120 has a rectangular rod shape and thus has four lateral faces including a first lateral face, a second lateral face adjacent to the first lateral face, a third lateral face adjacent to the second lateral face and opposite the first lateral face, and a fourth lateral face adjacent to the third lateral face and opposite the second lateral face. Separation points 120d are formed in two lateral faces from among the four lateral faces so that the two opposite lateral faces may be separated to form the two surfaces of the exit surface 120f. For example, two opposite lateral faces of the rod lens 120 may include a separation slit extending from the separation point 120d to the exit surface 120f. In one embodiment, the other two lateral faces of the rod lens 120 do not have a separation slit.

Figure 3C:
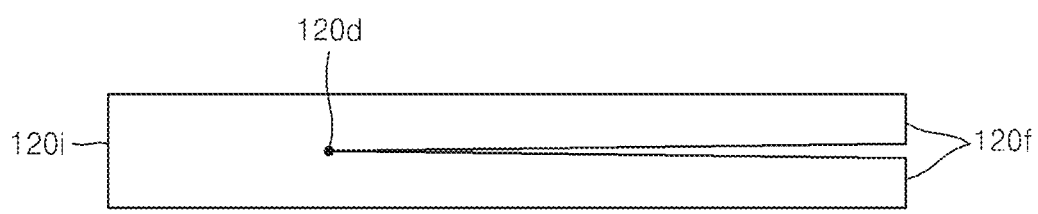
FIG. 3C is a lateral view of a rod lens for a lighting apparatus according to an embodiment of the inventive concept.

FIG. 3C is a lateral view of the rod lens 120 according to an embodiment of the inventive concept.

Referring to FIG. 3C, the incident surface 120i is formed of one surface. The rod lens 120 is branched off into two branches at the separation points 120d so that the exit surface 120f is formed to include two discontinuously separate surfaces. In FIGS. 3A through 3C, the separation points 120d are positioned closer to the incident surface 120i than the exit surface 120f of the rod lens 120 (e.g., in one embodiment, at a position one-fourth of the length of the lens away from the incident surface 120i). However, the separation points 120d may be located at other positions. For example, the separation points 120d may be formed to be closer to the center portion of the rod lens 120 or the exit surface 120f than the incident surface 120i. The separation points 120d may be positioned closer to the incident surface 120i than the center portion of the rod lens 120.

According to an embodiment, the rod lens 120 includes the exit surface 120f formed of two spaced apart surfaces having the same combined area as the area of the incident surface 120i formed of one continuous surface. The rod lens 120 separates and emits the light incident from the light source 110 into two parts of light via the exit surface 120f, and allows the separated two parts of light to correspond to the record region and the light irradiation region of the first light receiving unit 186a and the second light receiving unit 186b respectively, thereby preventing unnecessary light irradiation onto a shadow region, and inhibiting noise of light reflected from the shadow region, and thus, detectability of an examination device may be improved.

Figure 4:
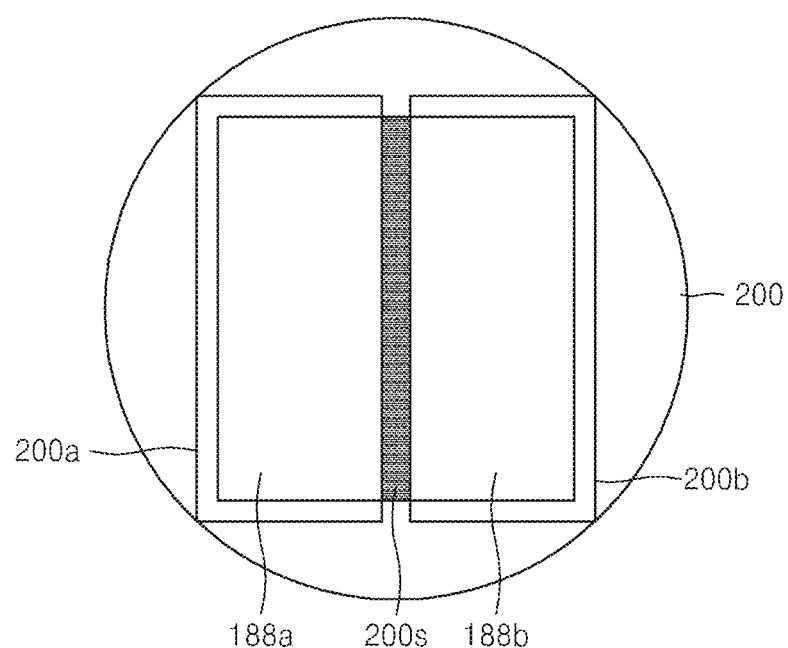
FIG. 4 is a diagram of a light irradiation region when light is irradiated onto an examination object by using a lighting apparatus including a rod lens and multiple light receiving units according to an embodiment of the inventive concept.

FIG. 4 is a diagram of a light irradiation region when light is irradiated onto the examination object 200 by using the lighting apparatus 102 including the rod lens 120 and multiple light receiving units according to an embodiment of the inventive concept.

A first light receiving unit recording region 188a whose image is recorded by the first light receiving unit 186a and a second light receiving unit recording region 188b whose image is recorded by the second light receiving unit 186b are formed in parallel within a range of vision of the objective lens 150. The first recording unit 188a and the second recording unit 188b have the same area or different areas. A shadow region 200s is formed between the first light receiving unit recording region 188a and the second light receiving unit recording region 188b within the range of vision of the objective lens 150. A first light irradiation region 200a is formed to include the first light receiving unit recording region 188a and to have substantially the same area as that of the first light receiving unit recording region 188a which is in the range of vision of the objective lens 150. A second light irradiation region 200b is formed to include the second light receiving unit recording region 188b and to have substantially the same area as that of the second light receiving unit recording region 188b which is in the range of vision of the objective lens 150. The first light irradiation region 200a and the second light irradiation region 200b are not formed in the shadow region 200s. As shown in FIG. 4, when the region recorded by multiple light receiving units is substantially the same as the light irradiation region on the examination object 200, the light coming from the light source 110 is not irradiated onto the shadow region 200s, thereby preventing unnecessary loss of light, and also reducing noise of light that would be caused by the light reflection from the shadow region 200s if the light were irradiated on the shadow region 200s. As a result, detectability of the lighting apparatus 102 and an examination device including the lighting apparatus 102 are improved.

Figure 5:
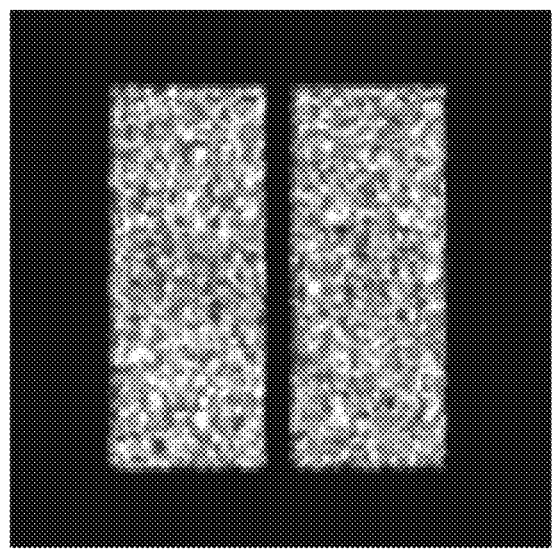
FIG. 5 is a simulated cross-sectional view of an examination object onto which light is irradiated by using a lighting apparatus including a rod lens and multiple light receiving units according to an embodiment of the inventive concept.

FIG. 5 is a simulated cross-sectional view of an examination object onto which light is irradiated by using the lighting apparatus 102 including the rod lens 120 and multiple light receiving units according to an embodiment of the inventive concept.

Referring to FIG. 5, no light is irradiated between the first light receiving unit recording region 188a and the second light receiving unit recording region 188b as shown in FIG. 4. It is dark similarly to the shadow region 200s in FIG. 4. The light is irradiated on the first light irradiation region 200a (see FIG. 4), which is substantially the same area as the first light receiving unit recording region 188a. The light is also irradiated on the second light irradiation region 200b (see FIG. 4), which is substantially the same area as the second light receiving unit recording region 188b. Therefore, the first light receiving unit recording region 188a and the second light receiving unit recording region 188b are bright.

As shown in the simulation result of FIG. 5, loss of light and noise of light are minimized by implementing separated light irradiation regions that are substantially identical to record regions of multiple light receiving units.

Figure 6:
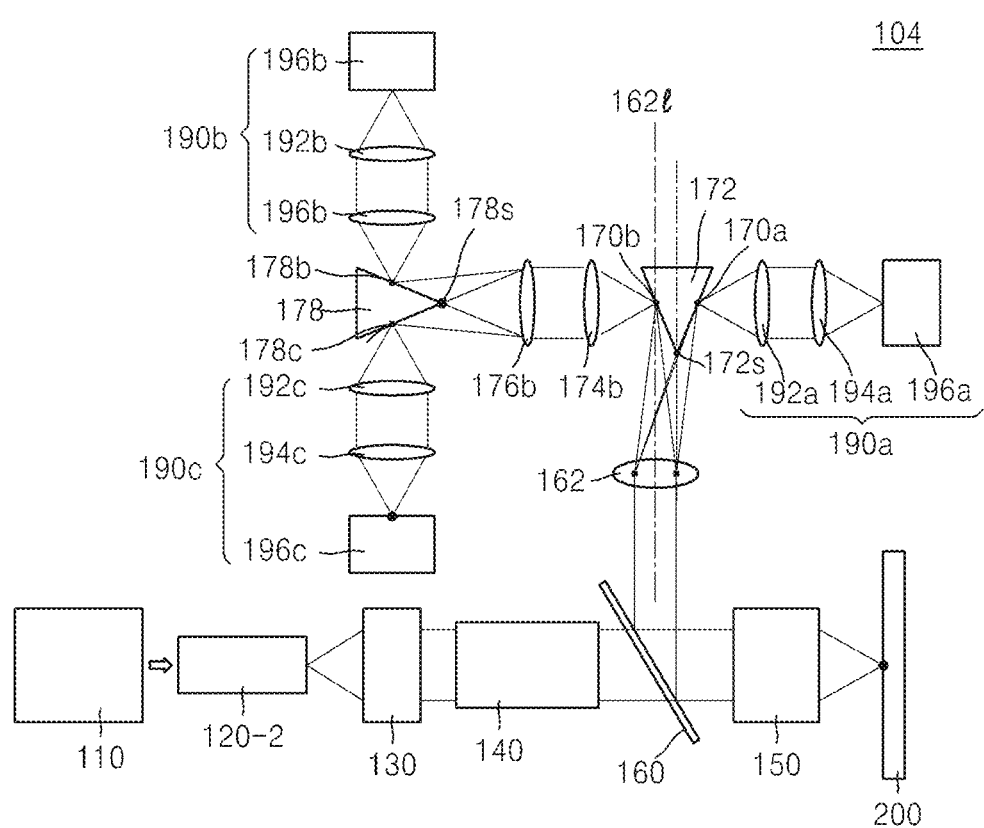
FIG. 6 is a conceptual diagram of a lighting apparatus including a rod lens and multiple light receiving units according to another embodiment of the inventive concept.

FIG. 6 is a conceptual diagram of a lighting apparatus 104 including a rod lens 120-2 and multiple light receiving units according to another embodiment of the inventive concept.

The lighting apparatus 104 includes a light source 110, the rod lens 120-2, a collimator 130, a relay unit 140, an objective lens 150, and a reflecting plate 160, like the lighting apparatus 102 of FIG. 2. The light source 110, the collimator 130, the relay unit 140, the objective lens 150, and the reflecting plate 160 are the same as those described with reference to FIG. 2 above, and thus descriptions thereof are not repeated.

The lighting apparatus 104 further includes a first polarization separation unit 172, a first focusing optics 190a, a second focusing optics 190b, a third focusing optics 190c, and a second polarization separation unit 178, in addition to the above elements.

The light source 110 generates light, and the light passes through the objective lens 150 via the rod lens 120-2, the collimator 130 and the relay unit 140. The light reaches and is reflected from the examination object 200, and then reaches the first polarization separation unit 172 via the reflecting plate 160. The first polarization separation unit 172 separates the light into polarized light and transfers the separated polarized light to the first focusing optics 190a and the second polarization separation unit 178.

According to an embodiment of the inventive concept, the first polarization separation unit 172 may be formed of a triangular prism. The triangular apex of the first polarization separation unit 172 is not formed in the center line 1621 extending from the center of the polarization separation lens 162. For example, the apex of the first polarization separation unit 172 is not positioned on the extension of the optical axis of the polarization separation lens 162. Therefore, the apex is deviated or obliquely disposed, for example, to the right of the optical axis or the center line 1621, which is different from that of FIG. 2. Thus, the light reflected by the reflecting plate 160 reaches the first polarization separation unit 172 such that a luminous flux of the polarized light separated via the polarization separation lens 162 may not be separated equally. For example, among the luminous flux of the polarized light separated via the polarization separation lens 162, the luminous flux of the polarized light reflected toward the second polarization separation unit 178 is higher than the luminous flux of the polarized light reflected toward the first focusing optics 190a.

For example, among the polarized light reflected from the first polarization separation unit 172, the polarized light reflected from a first surface 172a of the first polarization separation unit 172 is transferred to the first focusing optics 190a so that an image is formed on the first light receiving unit 196a. The polarized light reflected from a second surface 172b of the first polarization separation unit 172 is transferred to the second polarization separation unit 178 via a second light collection lens 174b and a second polarization light separation lens 176b. The polarized light reflected from a third surface 172s of the first polarization separation unit 172 is not transferred in a specific direction due to diffuse reflection, and is dispersed in many different directions because the polarized light reaches the apex of the prism. The polarized light reflected from the third surface 172s forms a first shadow region 202s (see FIG. 8), and no image is formed in the corresponding light receiving unit.

The first focusing optics 190a includes a first focusing lens 192a, a second focusing lens 194a, and a first light receiving unit 196a. The first focusing lens 192a parallelizes the path of the light collected on and reflected from the first surface 172a of the polarization separation unit 172 and allows the light to reach the second focusing lens 194a. The second focusing lens 194a collects the parallelized light transferred from the first focusing lens 192a to the first light receiving unit 196a. The first light receiving unit 196a may receive the light collected by the second focusing lens 194a and record the light as a partial surface of the examination object 200 corresponding to a first light receiving unit recording region 198a (see FIG. 8). The first light receiving unit 196a may be a CCD camera, a CMOS image sensor, or a LBCAST, like the first light receiving unit 186a of FIG. 2.

The polarized light reflected from the second surface 172b of the first polarization separation unit 172 is changed to parallel light via the second light collection lens 174b, is collected via the second polarization light separation lens 176b, and reaches the second polarization separation unit 178. The second polarization light separation lens 176b separates the parallel light into polarized light and allows the polarized light to reach the second polarization separation unit 178. The polarized light that reaches a first surface 178b of the second polarization separation unit 178 is reflected to the second focusing optics 190b and thus an image is focused on the second light receiving unit 196b. The polarized light that reaches a second surface 178c of the second polarization separation unit 178 is reflected to the third focusing optics 190c and thus an image is focused on the third light receiving unit 196c. The second light receiving unit 196b may record an image of a partial surface of the examination object 200 corresponding to a second light receiving unit recording region 198b (see FIG. 8). The third light receiving unit 196c may record an image of a partial surface of the examination object 200 corresponding to a third light receiving unit recording region 198c (see FIG. 8).

The configurations of the second focusing optics 190b and the third focusing optics 190c and a method of focusing an image on the second light receiving unit 196b and the third light receiving unit 196c are the same as described with reference to the first focusing optics 190a and the first light receiving unit 196a above, and thus descriptions thereof are not repeated.

Figure 8:
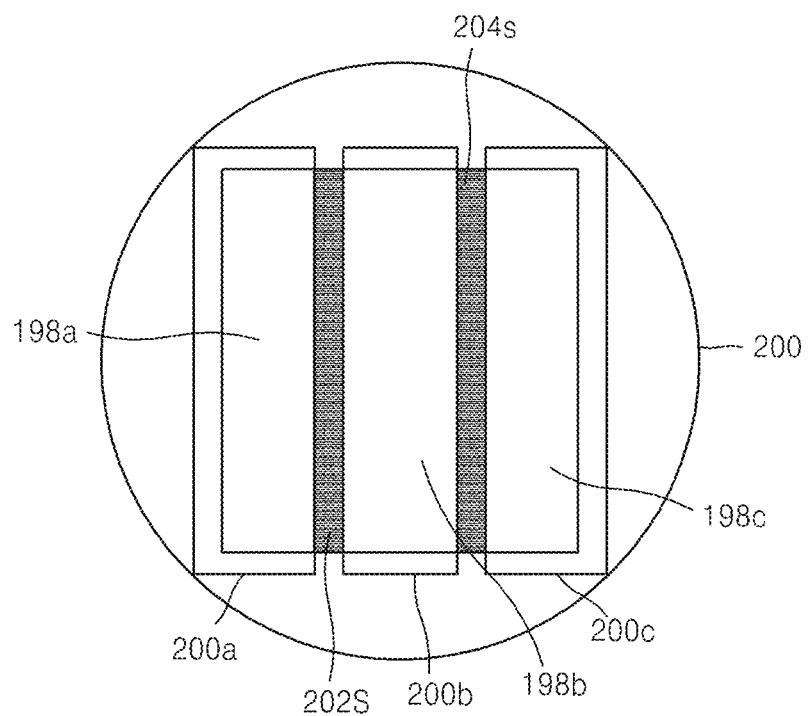
FIG. 8 is a diagram of a light irradiation region when light is irradiated onto an examination object by using a lighting apparatus including a rod lens and multiple light receiving units according to another embodiment of the inventive concept.

The polarized light that reaches a third surface 178s of the second polarization separation unit 178 via the second polarization light separation lens 176b is reflected in many different directions by an apex of a prism, thereby making diffuse reflection, and thus no image is focused on any of the first through third light receiving units 196a, 196b, and 196c. Thus, a second shadow region 204s of FIG. 8 is formed in the corresponding region that the polarized light reaches the third surface 178s.

As described with reference to FIG. 2, when the shadow region 204 is formed, loss of light occurs, light efficiency deteriorates, and, when the light irradiated onto the shadow region is reflected, reflection noise occurs. The lighting apparatus 104 includes three light receiving units including the first through third light receiving units 196a, 196b, and 196c, thereby forming a discontinuous exit surface of the rod lens 120-2 in consideration of position relationships of the first through third light receiving units 196a, 196b, and 196c and recording regions thereof on which the image is focused.

Figure 7A:
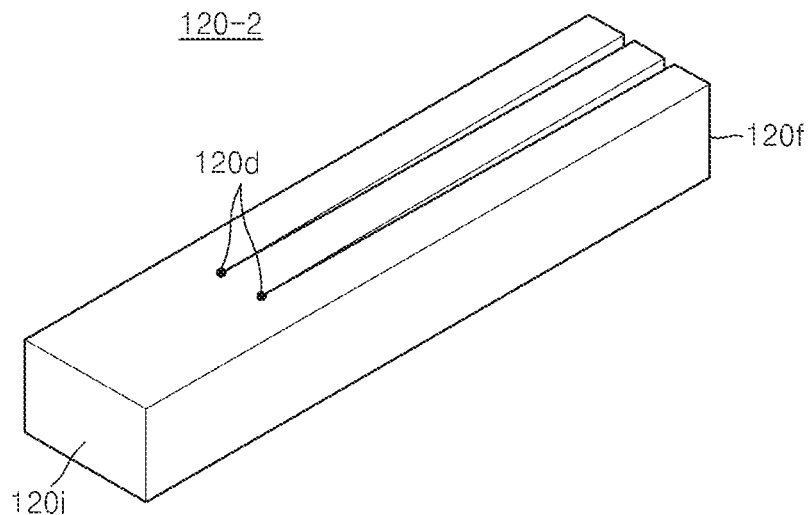
FIGS. 7A and 7B are perspective views of a rod lens for a lighting apparatus according to another embodiment of the inventive concept.
Figure 7B:
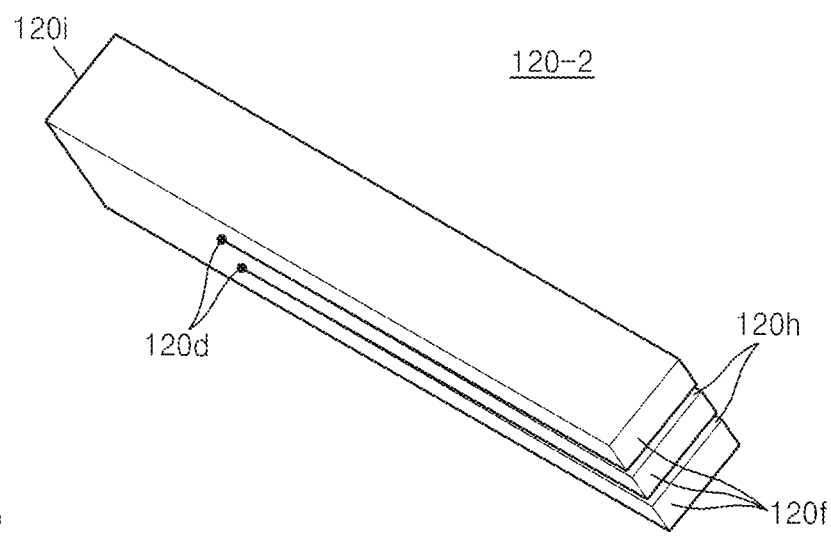

FIGS. 7A and 7B are perspective views of the rod lens 120-2 according to another embodiment of the inventive concept.

Referring to FIGS. 7A and 7B, the rod lens 120-2 is formed of a long rectangular rod having an incident surface 120i and an exit surface 120f shaped differently from each other. The incident surface 120i of the rod lens 120-2 is a surface through which light is incident from the light source 110 and forms one continuous rectangular plane. Meanwhile, the exit surface 120f includes two vertically separated openings 120h unlike the incident surface 120i, and includes three rectangular surfaces having the same areas separated by the openings 120h. The openings 120h may be formed in the positions corresponding to the shadow regions 202s and 204s (see FIG. 8). As shown in FIGS. 7A and 7B, the exit surface 120f of the rod lens 120-2 includes three rectangular surfaces having the same areas in one embodiment. The exit surface 120f of the rod lens 120-2 may be formed of surfaces having different areas according to positions of the first polarization separation unit 172 (see FIG. 6) and the second polarization separation unit 178 (see FIG. 6) and the light beam separation ratios thereof.

Figure 7C:
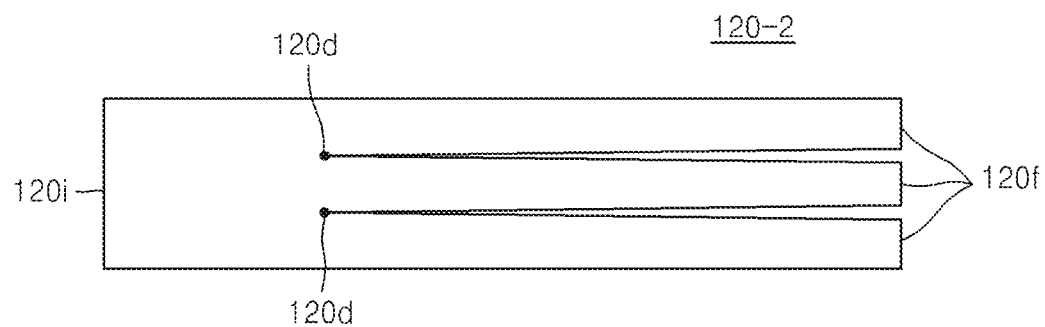
FIG. 7C is a lateral view of a rod lens for a lighting apparatus according to another embodiment of the inventive concept.

FIG. 7C is a lateral view of the rod lens 120-2 according one embodiment of the inventive concept.

Referring to FIG. 7C, the rod lens 120-2 includes two separation points 120d and three forked branches separated from the two separation points 120d. The two separation points 120d are formed to be more adjacent to the incident surface 120i than the exit surface 120f of the rod lens 120-2 in FIGS. 7A through 7C (e.g., in one embodiment, at a position one-fourth of the length of the lens away from the incident surface 120i). However, the two separation points 120d may be formed to be closer to the center portion of the rod lens 120-2 or the exit surface 120f than the incident surface 120i. The separation points 120d may be positioned closer to the incident surface 120i than the center portion of the rod lens 120-2.

FIG. 8 is a diagram of a light irradiation region when light is irradiated onto an examination object by using the lighting apparatus 104 including the rod lens 120-2 and multiple light receiving units.

The first, second and third light receiving unit recording regions 198a, 198b and 198c having the same area are formed in parallel within the range of vision of the objective lens 150. The first shadow region 202s is formed between the first light receiving unit recording region 198a and the second light receiving unit recording region 198b within the range of vision of the objective lens 150. The second shadow region 204s is formed between the second light receiving unit recording region 198b and the third light receiving unit recording region 198c within the range of vision of the objective lens 150. The first light irradiation region 200a is formed to surround the first light receiving unit recording region 198a and have substantially the same area as that of the first light receiving unit recording region 198a within the range of vision of the objective lens 150. The second light irradiation region 200b is formed to surround the second light receiving unit recording region 198b and have substantially the same area as that of the second light receiving unit recording region 198b within the range of vision of the objective lens 150. The third light irradiation region 200c having substantially the same area as that of the third light receiving unit recording region 198c is formed within the range of vision of the objective lens 150. As described with reference to FIG. 4, when the region recorded by the multiple light receiving units is substantially the same as the light irradiation region where the examination object 200 is irradiated by the light coming from the light source 110 via the rod lens 120-2, the light is not irradiated onto a shadow region, thereby preventing unnecessary loss of light, and also reducing reflection noise that would be caused by the light if it were reflected by the apexes of the triangular prism 172s and 178s, thereby improving detectability of the lighting apparatus 104 and an examination device including the lighting apparatus 104.

Figure 9A:
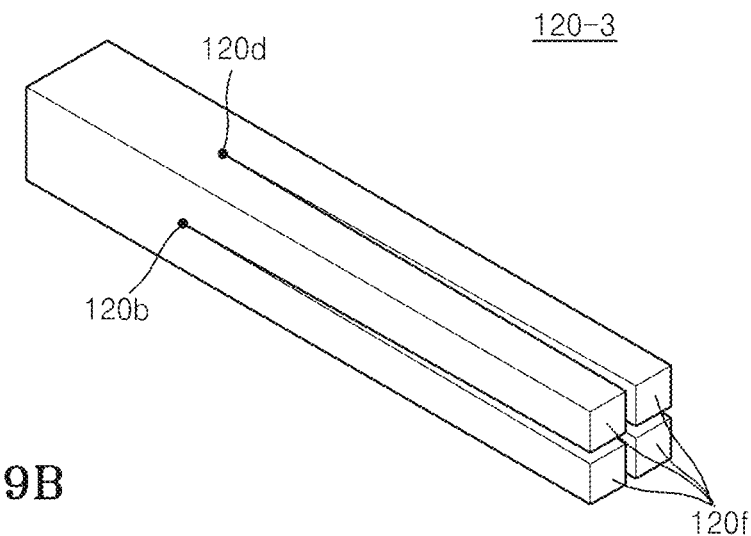
FIGS. 9A and 9B are perspective views of a rod lens for a lighting apparatus according to another embodiment of the inventive concept.
Figure 9B:
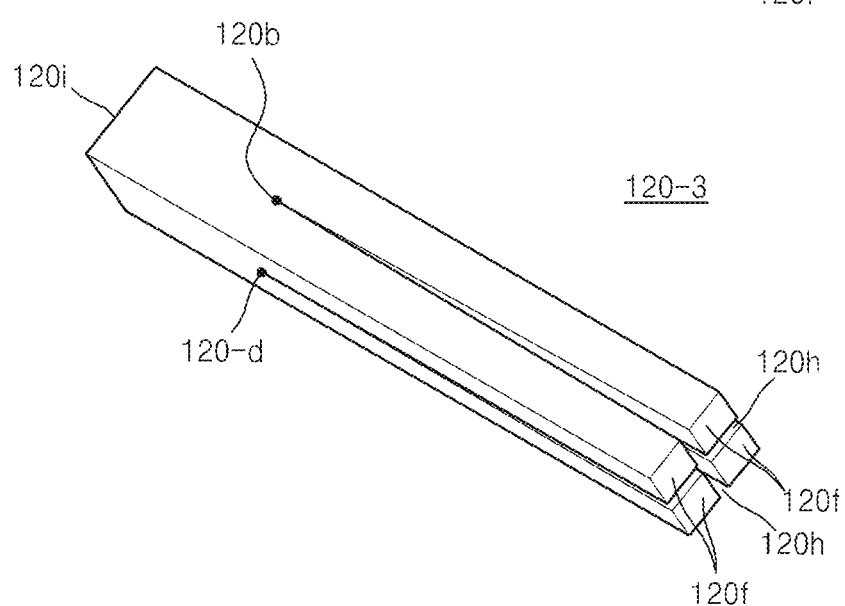

FIGS. 9A and 9B are perspective views of a rod lens 120-3 according to another embodiment of the inventive concept.

Referring to FIGS. 9A and 9B, the rod lens 120-3 is formed of a long rectangular rod which is similar to the rod lenses 120 and 120-2 as shown in FIGS. 3A and 7A. The rod lens 120-3 has an exit surface 120f and an incident surface 120i differently shaped from each other. The exit surface 120f has an opening 120h having a cross (+) shape which includes a vertical and a horizontal openings crossing each other. The exit surface 120f is formed to include four rectangular shape surfaces having the same area separated by the opening 120h. The opening 120h is formed to correspond to the positions of four light receiving units and the light beam separation ratio. For example, when a polarization separation device separates polarized light into four luminous fluxes, the opening 120h may be formed to correspond to the light beam separation ratios and positions of four light receiving units. The polarization separation device may have a cubic shape or another three dimensional shape. The lighting device may include multiple polarization separation devices to correspond the rod lens 120-3. For example, the lighting device may have three polarization separation devices to separate the light beam into four directions. No light is irradiated from the opening 120h of the rod lens 120-3 which corresponds to the shadow region 200s (see FIG. 10). The exit surface 120f of the rod lens 120-3 includes four rectangular surfaces having the same area in FIGS. 9A and 9B. The exit surface 120f may be formed to include different areas according to the structure and the shape of the polarization separation device and the light beam separation ratios thereof.

Figure 9C:
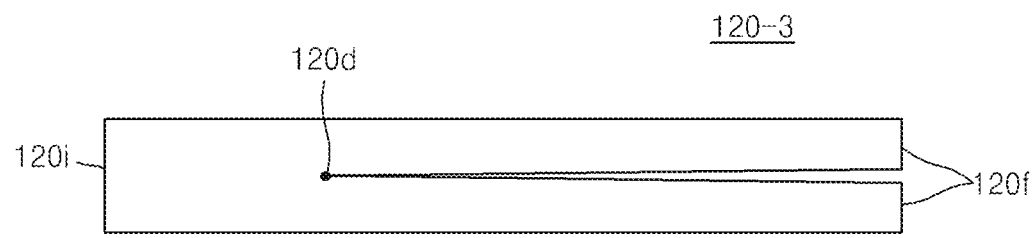
FIG. 9C is a lateral view of a rod lens for a lighting apparatus according to another embodiment of the inventive concept.

FIG. 9C is a lateral view of the rod lens 120-3 according to one embodiment of the inventive concept.

Referring to FIG. 9C, the separation points 120d are formed in four lateral faces of the rod lens 120-3 formed of a cuboid having four lateral faces. As shown in FIGS. 9A and 9B, a separation point 120d is formed on each of the lateral faces. The lateral faces of the rod lens 120-3 may be the same as those shown in FIG. 3C except for additional separation points in the rod lens 120-3. In FIGS. 9A through 9C, the separation points 120d are formed to be more adjacent to the incident surface 120i than the exit surface 120f of the rod lens 120-3 (e.g., in one embodiment, the separation points 120d may be at a position one-fourth of the length of the lens away from the incident surface 120i). The separation points 120d may be formed to be more adjacent to the center portion of the lens 120-3 or the exit surface 120f than the incident surface 120i in another embodiment. The separation points 120d may be positioned closer to the incident surface 120i than the center portion of the rod lens 120-3.

Figure 10:
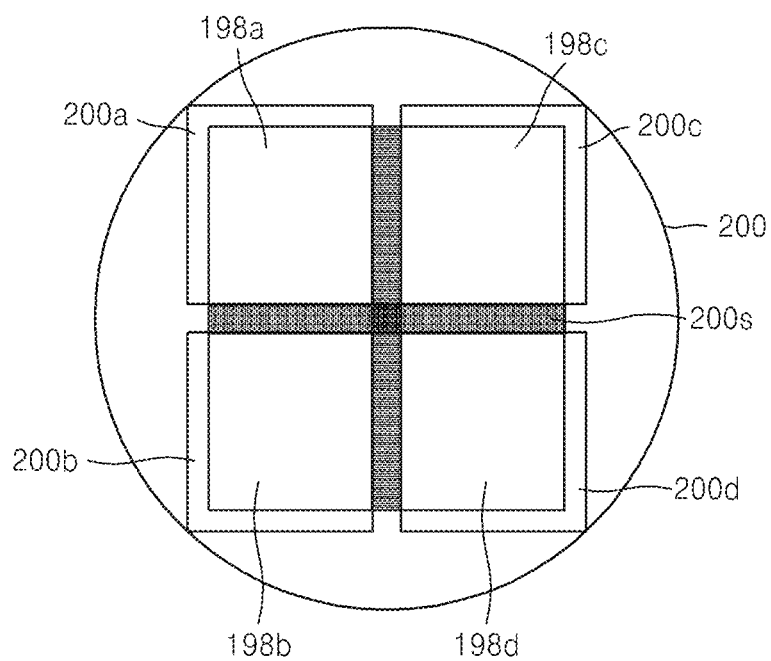
FIG. 10 is a diagram of light irradiation regions when a lighting apparatus including four light receiving units irradiates light onto an examination object via a rod lens according to another embodiment of the inventive concept.

FIG. 10 is a diagram of the light irradiation regions 200a through 200d when a lighting apparatus including four light receiving units irradiates light onto an examination object via the rod lens 120-3 according to one embodiment of the inventive concept.

Referring to FIG. 10, the four light receiving unit recording regions 198a through 198d having the same area are formed in a grid shape within the range of vision of the objective lens 150. The light irradiation regions 200a through 200d having substantially the same area are formed in the four light receiving unit recording regions 198a through 198d, respectively. The shadow region 200s having a cross (+) shape is formed between the four light receiving unit recording regions 198a through 198d. The shadow region 200s is a region that is not recorded on the light receiving units because diffuse reflection by a polarization separation device would cause reflection noise to the test result if the shadow region 200s were irradiated by the light. The shadow region 200s corresponds to the opening 120h (see FIG. 9B) of the rod lens 120-3.

Lighting apparatuses 102 and 104 are used to examine, for example, patterns formed by a photolithography process including manufacturing semiconductor devices, liquid crystal displays, etc. The lighting apparatuses 102 and 104 may include one of the rod lenses described above.

An exemplary method of manufacturing a semiconductor device is described hereinafter, according to one embodiment of the present disclosure. The manufacturing process of a semiconductor device may include steps forming semiconductor patterns, insulator patterns and metal patterns on a substrate. The patterned substrates are examined to determine whether the patterns are properly formed. In this case, lighting apparatuses 102 and 104 are used to examine the patterns. The lighting apparatuses 102 and 104 may have an examination platform. The substrate as an examination object is mounted on the examination platform of a lighting apparatus. A pattern in a first portion of the substrate is examined. It is determined whether the first pattern is proper or not, for example, pass or fail.

The light coming out from the exit surface of the rod lens may irradiate on the substrate, and a shadow region may be formed between the irradiated light patterns as shown in FIGS. 4, 8 and 10.

The recorded image by the plurality of light receiving units may form a shadow region which corresponds to the substrate not recorded by the light receiving units and which is between the regions recorded by the light receiving units.

Therefore, the shadow regions 200s, 202s and 204s are examined in a second examination step. In this case, a second pattern examined in the second examination step may overlap the first pattern to make sure that there is no pattern omitted from the examination. If a pattern is determined to pass, then the device including the pattern (e.g. a semiconductor chip) may be further processed (e.g. by encapsulation) and formed into an electronic device (e.g. a semiconductor chip package).

While the disclosure has been particularly shown and described with reference to exemplary embodiments thereof, it will be understood that various changes in form and details may be made therein without departing from the spirit and scope of the disclosure. The scope of the invention should be interpreted by the language of the following claims.

What is claimed is:

1. A rod lens for a lighting apparatus, the rod lens having a rectangular rod structure extending lengthwise comprising:
   a first end and a second end opposing each other;
   a first lateral face;
   a second lateral face adjacent to the first lateral face;
   a third lateral face adjacent to the second lateral face and opposite the first lateral face; and
   a fourth lateral face adjacent to the third lateral face and opposite the second lateral face,
   wherein the first end is formed of one continuous surface, the second end is formed of a plurality of separated surfaces, the first end is a light incident surface of the lens, and the second end is a light exit surface of the lens,
   wherein parts of the first lateral face and the third lateral face are separated to correspond to the plurality of separated surfaces of the second end, and each of separation points starting the separated lateral faces is disposed between the first end and a center of the rod lens,
   wherein each of the separation points is a shape of a vertex in the first lateral face and the third lateral face.

2. The rod lens of claim 1, wherein the second end has two surfaces having the same area.

3. The rod lens of claim 1, wherein the second end is separated to have three surfaces having the same area.

4. The rod lens of claim 1, wherein the second end is separated to have four surfaces having the same area.

5. A lighting apparatus comprising:
   a light source for emitting light;
   a rod lens positioned to receive the light through an incident surface and send out the light through an exit surface;
   an objective lens facing an examination object; and
   a plurality of light receiving units positioned to receive light reflected from the examination object and record an image of the examination object,
   wherein the incident surface of the rod lens is formed of one continuous surface,
   the exit surface of the rod lens is separated into a plurality of surfaces,
   a combined area of the plurality of separated surfaces is substantially the same as an area of the one continuous surface,
   a space is positioned between two immediately adjacent surfaces of the plurality of separated surfaces, and wherein the rod lens comprises:
a first lateral face;
a second lateral face adjacent to the first lateral face;
a third lateral face adjacent to the second lateral face and opposite the first lateral face; and
a fourth lateral face adjacent to the third lateral face and opposite the second lateral face,
wherein parts of the first lateral face and the third lateral face are separated to correspond to the plurality of separated surfaces of the exit surface, and each of separation points starting the separated lateral faces is disposed between the incident surface and a center of the rod lens.

6. The lighting apparatus of claim 5, wherein the plurality of light receiving units comprises two light receiving units, wherein the exit surface of the rod lens is separated into two parts, and each of the two parts corresponds to one of the two light receiving units.

7. The lighting apparatus of claim 6, wherein the two parts of the exit surface of the rod lens have the same area.

8. The lighting apparatus of claim 5, wherein the plurality of light receiving units comprises three light receiving units, wherein the exit surface of the rod lens is separated into three parts, and each of the three parts corresponds to one of the three light receiving units.

9. The lighting apparatus of claim 8, wherein the three parts of the exit surface of the rod lens have the same area.

10. The lighting apparatus of claim 5, wherein the plurality of light receiving units comprises four light receiving units, wherein the exit surface of the rod lens is separated into four parts, and each of the four parts corresponds to one of the four light receiving units.

11. The lighting apparatus of claim 10, wherein the exit surface of the rod lens is vertically and horizontally separated so as to have four parts having the same area.

12. A rod lens for a lighting apparatus, the rod lens having a rectangular rod structure extending lengthwise comprising a first end and a second end opposing each other,
wherein the first end is formed of one continuous surface, the second end is formed of a plurality of separated surfaces, the first end is a light incident surface of the lens, and the second end is a light exit surface of the lens,
wherein the rod lens comprises separation points formed in two opposite lateral faces so that the two opposite lateral faces are separated to form the plurality of separated surfaces of the second end, and the rod lens is formed of a continuous body, and
a space is positioned between two immediately adjacent surfaces of the plurality of separated surfaces,
wherein each of the separation points starting the separated lateral faces is disposed between the first end and a center of the rod lens.

13. The rod lens of claim 12, wherein a combined area of the plurality of separated surfaces is substantially the same as an area of the one continuous surface.

14. The rod lens of claim 12, wherein the two opposite lateral faces of the rod lens comprise a separation slit extending from the separation points to the second end.

15. The rod lens of claim 14, wherein two other lateral faces of the rod lens are continuous surfaces.

16. The rod lens of claim 12, wherein the two opposite lateral faces of the rod lens comprise a separation slit extending from the separation points to the second end.

17. The rod lens of claim 12, wherein the two opposite lateral faces of the rod lens comprise a separation slit extending from the separation points to the second end.

* * * * *